United States Patent [19]

Fujita et al.

[11] Patent Number: 5,239,861
[45] Date of Patent: Aug. 31, 1993

[54] DEVICE FOR INDICATING CONTAMINATION DEGREE OF HYDRAULIC CIRCUIT AND METHOD OF JUDGING THE CONTAMINATION DEGREE

[75] Inventors: Nobuo Fujita, Uji; Nobuaki Nakarai, Kawaguchi, both of Japan

[73] Assignee: Kabushiki Kaisha Komatsu Seisakusho, Tokyo, Japan

[21] Appl. No.: 566,452

[22] PCT Filed: Dec. 12, 1989

[86] PCT No.: PCT/JP89/01285

§ 371 Date: Jan. 16, 1991

§ 102(e) Date: Jan. 16, 1991

[87] PCT Pub. No.: WO90/07706

PCT Pub. Date: Jul. 12, 1990

[30] Foreign Application Priority Data

Dec. 23, 1988 [JP] Japan ............... 63-325536
Feb. 28, 1989 [JP] Japan ............... 1-44089
Feb. 28, 1989 [JP] Japan ............... 1-46988

[51] Int. Cl.⁵ .......................................... G01N 15/00
[52] U.S. Cl. ...................... 73/61.73; 116/DIG. 42; 340/607
[58] Field of Search ............ 73/61 R, 61.4 R, 38 R, 73/28.06, 865.5, 61.73; 340/607; 116/DIG. 42, DIG. 25

[56] References Cited

U.S. PATENT DOCUMENTS

| | | | |
|---|---|---|---|
| 2,390,539 | 12/1945 | Katcher | 116/DIG. 42 X |
| 3,203,253 | 8/1965 | Scheid | 73/61 R X |
| 3,357,236 | 12/1967 | Kasten | 73/61 R |
| 3,511,382 | 5/1970 | Mesek | 73/61 R X |
| 3,709,614 | 1/1973 | Hayakawa | 73/865.5 X |
| 4,117,715 | 10/1978 | Hoenig | 73/28 |
| 4,583,396 | 4/1986 | Hunt et al. | 73/61 R |
| 4,685,066 | 8/1987 | Hafele et al. | 364/509 |
| 5,095,740 | 3/1992 | Hodgson et al. | 73/61 R |

FOREIGN PATENT DOCUMENTS

| | | |
|---|---|---|
| 52-129579 | 10/1977 | Japan . |
| 58-4779 | 1/1983 | Japan . |
| 60-262040 | 12/1985 | Japan . |
| 62-070732 | 4/1987 | Japan . |

OTHER PUBLICATIONS

Patent Abstracts of Japan, vol. 10, No. 143 (P-459) [2200], published May 27, 1986, re JP-A-60-262,040.
Patent Abstracts of Japan, vol. 11, No. 264 (P-610) [2711], published Aug. 27, 1987, re JP-A-62-070,732.

Primary Examiner—Hezron E. Williams
Assistant Examiner—Joseph W. Roskos
Attorney, Agent, or Firm—Richards, Medlock & Andrews

[57] ABSTRACT

Two or more filters of different filtration particle size capabilities are arranged in a hydraulic circuit such that hydraulic oil containing contaminants is passed through the filters, either in series according to the order of the filtration particle size capability or in parallel. A sensor determines the pressure differential between the inlet and outlet of a respective filter, and a signal is provided to a contamination level indication device when the pressure differential between the inlet and outlet of a respective filter exceeds a predetermined level.

20 Claims, 6 Drawing Sheets

DEVICE FOR INDICATING CONTAMINATION DEGREE OF HYDRAULIC CIRCUIT AND METHOD OF JUDGING THE CONTAMINATION DEGREE

TECHNICAL FIELD

The present invention relates to a device for indicating the degree of contamination of a hydraulic circuit and a method of judging the degree of contamination. More particularly, the present invention is concerned with a device for indicating the contamination degree and a method of judging the contamination degree suitable for use in a hydraulic circuit which incorporates a filtering device having filters of different filtration particle sizes, such as a hydraulic circuit in an industrial vehicle or a vehicle used in construction, e.g., a power shovel.

BACKGROUND OF THE INVENTION

In general, a hydraulic circuit on an industrial vehicle or a construction vehicle such as a power shovel incorporates a filtering device having filters. The filtering device has a device for indicating the degree of contamination which displays the timing of renewal or cleaning of filters or timing of renewal of contaminated oil, thereby preventing occurrence of troubles in the hydraulic system.

Figure 9:
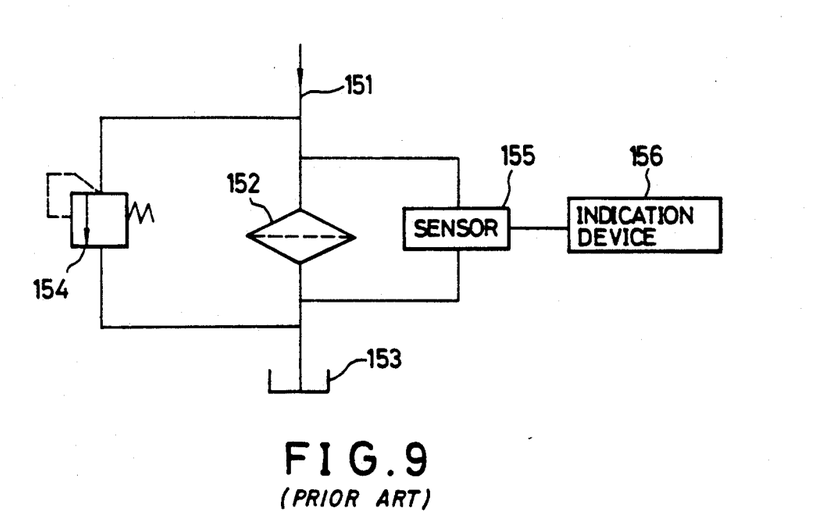
FIG. 9 is an illustration of the general arrangement of a prior art.

The contamination degree indicating device used in this type of hydraulic circuit has to cope with a wide distribution of the sizes of contaminant particles in the oil, from substantially 0 to several hundreds of μm. Such a hydraulic circuit employs one or a plurality of filters of the same mesh, e.g., a capability to trap particles of 20 to 30 μm, each filter being provided with a contamination degree indicating device capable of indicating the degree of clogging of the filter. As shown in FIG. 9, oil returning from an actuator or a hydraulic motor flows to an oil tank 153 through a return passage 151 via a filter 152. Contaminants in the oil, therefore, are trapped by the filter 152. As the amount of contaminants accumulated on the filter increases, the clogging of the filter becomes heavier so that a greater flow resistance is produced by the filter, with the result that the oil pressure rises at the inlet side of the filter. In consequence, a bypass valve 154 is opened to cause the oil to flow into the oil tank 153 bypassing the filter 152. Thus, when the amount of contaminants in the oil increases to cause a heavier clogging of the filter, the pressure differential between the inlet and outlet sides of the filter is increased correspondingly, so that the degree of clogging of the filter can be known through indication of the level of the pressure differential. A pressure sensor 155 is arranged to operate when the pressure differential between the inlet side and the outlet side of the filter reaches a predetermined level, and an indicating device 156 performs indication in response to a signal from the pressure sensor 155. The indication is usually conducted in advance of the opening of the bypass valve 154. The user replaces or cleans the filter or renews the contaminated oil upon recognition of the indication.

In the conventional system described above, the filter traps all the contaminant particles of sizes which widely vary between 20 or 30 μm to several hundreds of μm, and the indication is conducted when the pressure differential across the filter has reached a predetermined level. Thus, it is impossible to discriminate between the sizes of the contaminant particles. Namely, when particles of comparatively large sizes are being generated and contained in the oil, the indication device does not operate while the pressure differential is still low, often resulting in a breakdown of the hydraulic system.

Accordingly, an object of the present invention is to provide a device for indicating the degree of contamination of a hydraulic circuit and a method of judging the degree of contamination, wherein the states of clogging of filters are indicated at proper timings according to the sizes of the contaminant particles in the oil, thereby preventing breakdown of the hydraulic system.

SUMMARY OF THE INVENTION

To these ends, according to one aspect of the present invention, there is provided a device for indicating the degree of contamination of a hydraulic circuit, comprising: sensors arranged to operate when pressure differentials between inlets and outlets of filters disposed in a circuit of a working oil exceed predetermined values; and an indication device which operates in accordance with signals from the sensors, so that the states of clogging of the filters caused by contaminants in the working oil are detected through detection of the pressure differentials between the inlets and outlets of the filters and indicated by the indication device; with the improvement being that two or more filters of different filtration particle sizes are arranged and pressures at the inlets and outlets of the filters are measured, and, when the pressure differential between the inlet and the outlet has exceeded a predetermined reference value across one of the filters, an indicator unit of the indication device corresponding to the filter operates.

According to a second aspect, the two or more filters are connected in series according to the order of the filtration particle size, such that the filter of the greatest filtration particle size is disposed upstream of the filter of a medium filtration particle size which is upstream of the filter of the smallest filtration particle size. Alternatively, a shunt valve is provided in the hydraulic circuit so as to divide the flow of the working oil into two parallel lines and the two or more filters are arranged in the parallel lines of working oil. According to a third aspect, the device for indicating the degree of contamination of a hydraulic circuit further comprises a controller capable of performing computation on the basis of the pressure signals from the inlets and outlets of the filters and instructing the indication device to indicate the results of computation. Alternatively, the device for indicating the degree of contamination of a hydraulic circuit further comprises orifices arranged in the parallel lines in which the filters are arranged, sensors adapted to operate when the pressure differentials between the inlets and outlets of the respective orifices have reached predetermined values, and a controller capable of computing the state of clogging of the filters upon receipt of the signals from the sensors and delivering signals to the indication device. The flow rate of the working oil through the shunt valve is maintained constant by a flow rate control valve which is disposed in an inlet circuit of a filter provided in the hydraulic circuit.

According to a first form of the method of the invention for judging the degree of contamination, a working oil is made to flow successively through filters arranged in a circuit of a working oil in the order of the filtration particle size such that the filter of the greatest filtration particle size is disposed most upstream of the series of filters, and, when pressure differential between the inlet and outlet of one of the filters has exceeded a predetermined reference value, one of the sensors associated with the filter produces a pressure signal by means of which the state of the hydraulic circuit is judged and indicated as being safe, caution or abnormal. In a second form of the method of the invention, the degree of contamination in a hydraulic circuit is detected by detecting the states of clogging in filters provided in a circuit of a working oil, wherein the flow of the working oil is divided into two parts which flow through separate lines having filters of different filtration particle sizes and orifices, and the state of clogging of the filter in one of the lines is detected through sensing the pressure differential across the associated orifice and then the state of clogging of the filter in the other line is detected, the detection results being analyzed to classify the degree of contamination into at least three stages and indicated in terms of these stages.

Thus, according to the present invention, filters of different filtration particle sizes are arranged in a circuit of working oil of a hydraulic system, and pressure differentials across the respective filters or pressure differentials of orifices connected in the circuit are detected and indicated independently. It is therefore possible to conduct an early detection of comparatively large particles of foreign matters which tend to cause breakdown of the hydraulic system, and to grasp the degree of contamination of the working oil, thus enabling the user to take necessary countermeasure for preventing occurrence of troubles in the hydraulic system.

THE BEST MODE FOR CARRYING OUT THE INVENTION

Embodiments of the contamination degree indication device and the contamination degree judging method for a hydraulic circuit in accordance with the present invention will be described in detail with reference to the drawings.

Figure 1:
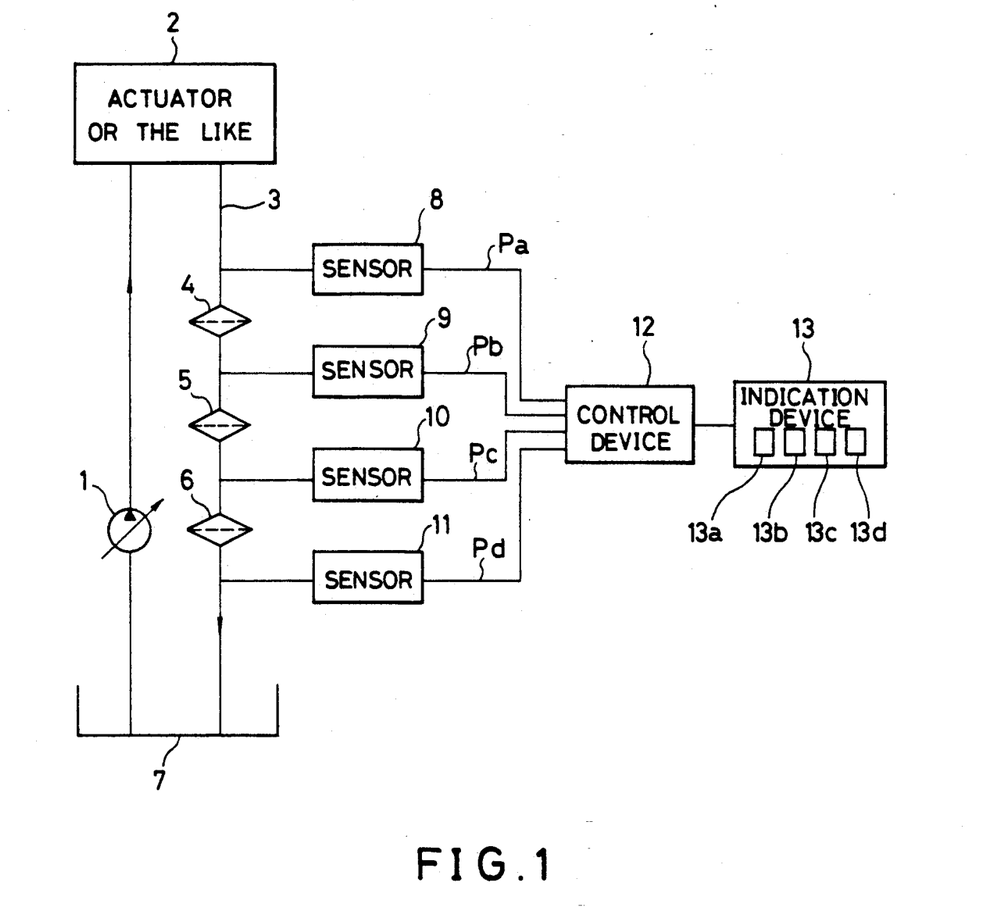
FIG. 1 is an illustration of the general arrangement of a first embodiment of the present invention.

FIG. 1 is an illustration of the general arrangement of a first embodiment.

Figure 2:
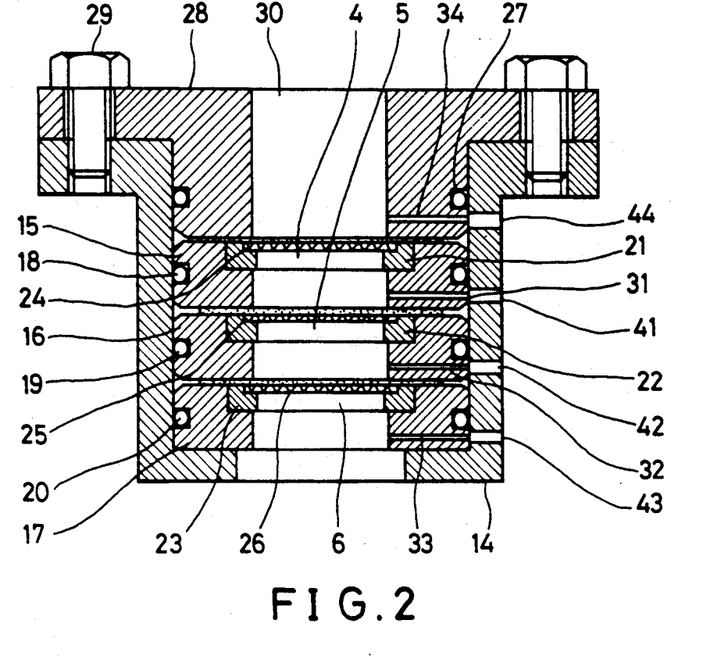
FIG. 2 is a sectional view showing a filter portion.

Referring to FIG. 1, a working oil displaced by a pump 1 is made to pass through a change-over valve which is not shown, and is delivered to, for example, an actuator 2 via a filter or through another change-over valve. The returning oil from, for example, the actuator flows back to an oil tank 7 through a series of filters 4, 5 and 6. As shown in FIGS. 1 and 2, the filters 4, 5, and 6 are in operation simultaneously. The filters 4, 5 and 6 have different mesh sizes, i.e., different filtration particle sizes. Representing the sizes of particles retained by the filters 4, 5 and 6 by $K_1$, $K_2$ and $K_3$, the filters are arranged to meet the condition of $K_1 > K_2 > K_3$. Pressure sensors 8, 9, 10 and 11 are disposed at the inlet and outlet sides of the filters 4, 5 and 6 as illustrated and the outputs of these pressure sensors are connected to a controller 12 to which is connected also an indication device 13. The indication device 13 is provided with a plurality of indicator units 13a, 13b, 13c and 13d which operate in accordance with the results of computation performed by the controller 12 in response to the signals from the pressure sensors 8, 9, 10 and 11 so as to indicate the state of the hydraulic system when one or more of the filters 4, 5 and 6 have been clogged.

FIG. 2 is a front elevational view of the filters used in the invention, i.e., the construction of the filters 4, 5 and 6 shown in FIG. 1. The filters have a case 14 having a bottom plate with a central aperture and plates 15, 16 and 17 which are provided with central apertures and received in the case 14. O-rings 18, 19 and 20 are placed between the plates 14, 15 and 16 and the wall of the case 14 so as to prevent oil flowing therethrough.

Rings 21, 22 and 23 are embedded in the plates and metal gauze wires 24, 25 and 26 are welded to these rings. The filters 5 and 6 are clamped between the plates 15, 16 and 17 as illustrated and the filter 4 is clamped between the plate 15 and a cover 28 having an O-ring 27. The cover 28 is fixed to the case 14 by means of bolts 29. The oil flows downwardly through the passageway 30 in the direction of an arrow. The filters 4, 5 and 6 are stably supported by the metal gauze wires 24, 25 and 26 so as not to be deformed by the fluid dynamical force of the oil. Representing the sizes of particles retained by the filters 4, 5 and 6 by $K_1$, $K_2$ and $K_3$, the filters are arranged to meet the condition of $K_1 > K_2 > K_3$. Oil pressures generated in the spaces defined by the plates 15, 16 and 17 and the cover 28 are transmitted to the pressure sensors through holes 31, 32, 33 and 34 and then through ports 41, 42, 43 and 44 Which are formed in the wall of the case 14.

The operation of the described device is as follows. Pressures Pa, Pb, Pc and Pd at the inlets and outlets of the filters 4 to 6 are picked up by the pressure sensors and are delivered to the controller 12 which computes the pressure differentials Ha (Ha=Pa−Pb), Hb (Hb=Pb−Pc) and Hc (Hc=Pc−Pd). The controller 12 then compares these pressure differentials with reference values Za, Zb and Zc of the pressure differentials across the respective filters, and enables the indicator units 13a, 13b, 13c and 13d to indicate the states, e.g., safe, caution I, caution II and abnormal, in accordance with a process which is shown by a flow chart in FIG. 3.

Figure 3:
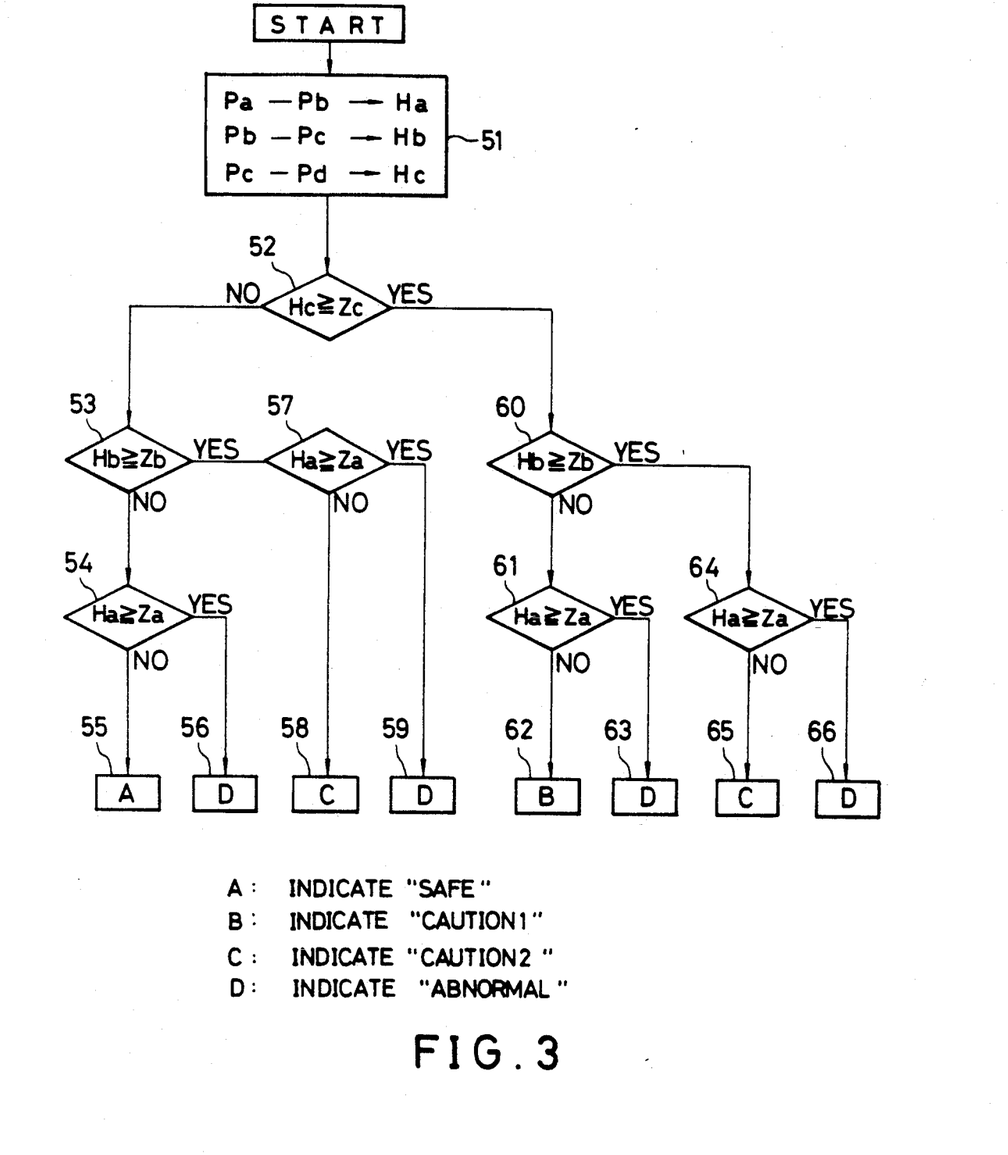
FIG. 3 is a flow chart of operation of the first embodiment.

Referring to FIG. 3, Step 51 executes computation of the pressure differentials on the basis of the signals from the pressure sensors 8 to 11. In Step 52, the pressure differential Hc is compared with the reference value Zc of the pressure differential for the filter 6. If the pressure differential Hc is smaller than the reference value Zc, the process proceeds to Step 53 in which the pressure differential Hb is compared with the reference value Zb. If the pressure differential Hb is below the reference value Zb, the process proceeds to Step 54 in which the pressure differential Ha computed for the filter 4 is compared with the reference value Za. If the pressure differential Ha is below the reference value Za, the safe state (symbol A: SAFE in FIG. 3) is indicated in Step 55. However, if the pressure differential Ha is found to be greater than the reference value Za, the process proceeds to Step 56 which is the abnormal state (symbol D: ABNORMAL in FIG. 3). In Step 53, when the pressure differential Hb across the filter 5 is greater than the reference value Zb, the process proceeds to Step 57 in which the pressure differential Ha across the filter 4 is compared with the reference value Za. If the comparison executed in Step 57 has proved that the pressure differential Ha is below the reference value Za, the process proceeds to Step 58 in which the caution II (symbol C, CAUTION 2 in FIG. 3) is indicated. Conversely, if the pressure differential Ha is greater than the reference value Za, the process proceeds to Step 59 in which the abnormal state (symbol D) is indicated. When the comparison conducted in Step 52 has proved that the pressure differential Hc across the filter 6 is greater than the reference value Zc, the process proceeds to Step 60 to successively conduct comparing operations 60, 61, 64. Indication of caution I (symbol B) in Step 62, indication of abnormal state (symbol D) in Steps 63, 66 and indication of caution II (symbol C) are executed in accordance with the results of these comparing operations. Thus, when large particles of foreign matters are generated in the hydraulic system, such particles, when the particle size exceeds $K_1$, are trapped by the filter 4 the state of which is detected by the sensors 8 and 9 so that abnormality is indicated. Ordinary fine contaminant particles are trapped by the filter 6. The indication device 13 indicates the safe state while the amount of such particles on the filter 6 is still below a predetermined amount but, when the reference value of the pressure differential across the filter 6 is exceeded, the indication device 13 indicates caution.

Figure 4:
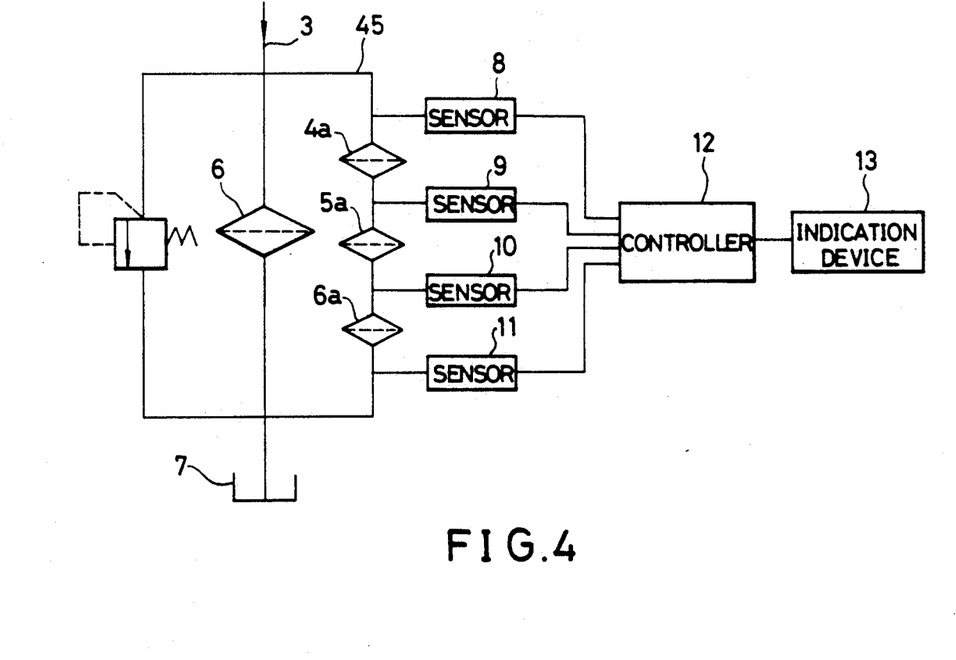
FIG. 4 is an illustration of the general arrangement of a second embodiment of the present invention.

FIG. 4 shows a second embodiment of the present invention. In this Figure, the same reference numerals are used to denote the same components as those in FIG. 1 and description of such components is omitted. This embodiment has a series of detection filters 4a, 5a and 6a which are arranged in the order of the trapping particle size as in the first embodiment. An ordinary filter 6 is disposed in parallel with the series connection of the detection filters 4a, 5a and 6a. As shown in FIG. 4, the filters 4a, 5a, and 6a are in operation simultaneously.

In operation, the working oil from the return passage 3 partly flows through the filter 6 and partly through the series of detection filters 4a, 5a and 6a. As foreign matters are trapped by the filter 6, the pressure rises at the inlet side of the filter 6 so that the flow rate of the oil flowing through the series of detection filters 4a, 5a and 6a is increased with the result that the resistance through the circuit 45 is increased, thus maintaining the balance of flow rate.

Figure 5:
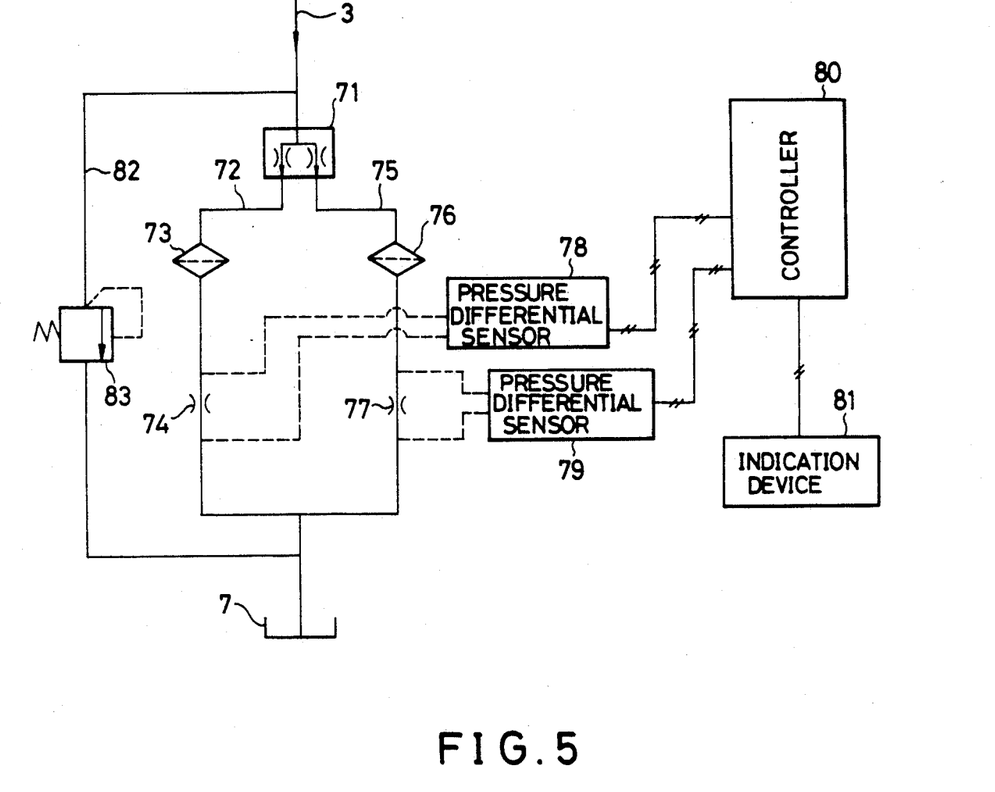
FIG. 5 is an illustration of the general arrangement of a third embodiment of the present invention.
Figure 6:
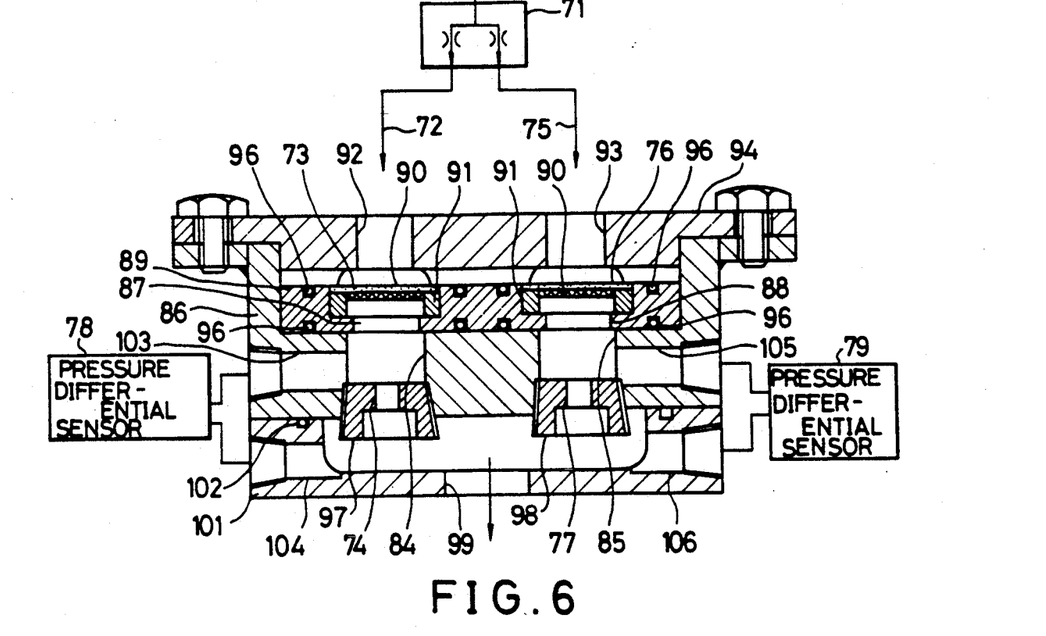
FIG. 6 is a sectional front elevational view showing a filter portion and an orifice portion.

FIG. 5 is an illustration of the general arrangement of a third embodiment. Working oil returning from an actuator or a hydraulic motor which is not shown is made to flow through the return passage 3 and is branched into two portions by a shunt valve 71: namely, a portion which returns to the oil tank 7 through a conduit 72 containing a filter 73 and an orifice 74, and another portion which returns to the oil tank 7 through a conduit 75 containing a filter 76 and an orifice 77. As shown in FIGS. 5 and 6, the filters 73 and 76 are in operation simultaneously. Which one of the filter and the orifice is disposed on the upstream side of the other does not matter in each case. The filtration particle sizes of the filters 73 and 76 are respectively represented by $K_1$ and $K_1$ which are determined to meet the condition of $K_1 > K_2$. The inlet and outlet sides of the orifices 74 and 77 are communicated with the pressure sensors 78 and 79 connected to a controller 80 to which is connected also an indication device 81. A conduit 82 parallel to the filter circuit has a bypass valve 83.

FIG. 6 is a front elevational sectional view of a portion of the embodiment shown in FIG. 5 including the filters 73, 76 and the orifices 74, 77. A plate 89 having two apertures 87 and 88 is received in a case 86 which also has two apertures 84, 85. The plate 89 has a pair of rings 91, 91 to which are welded metal gauze wires 90, 90. These rings are embedded to cover the apertures 87, 88 and the filters 73 and 76 are disposed on these metal gauze wires 90, 90. A cover 94 has apertures 92, 93 respectively communicating with conduits 72, 75 through which the flows of oil divided by the shunt valve 71 are led. The plate 89 is clamped between the cover 94 and case 86 such that the apertures 84, 87 and 92 are aligned with each other and the apertures 85, 88 and 93 are aligned with each other. O rings 96 are provided to prevent leakage of the oil. Plugs 97 and 98 having the orifices 74 and 77 are mounted in the apertures 84 and 85 in the case 86. A lower cover 101 having a central oil outlet port 99 in the bottom thereof is fixed by bolts or the like to the case 86 through the intermediary of an O-ring 102 which prevents oil from leaking to the outside. A port 103 formed in the case 86 and a port 104 formed in the lower cover 101 are communicated with a pressure differential sensor 78, while ports 105 and 106 are connected to the pressure differential sensor 79.

Figure 7:
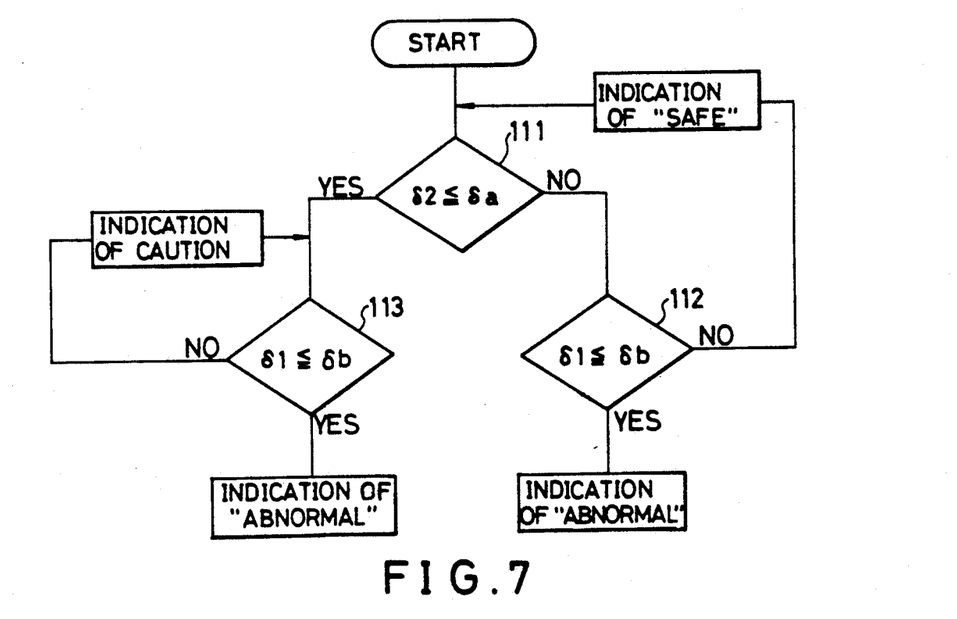
FIG. 7 is a flow chart showing the operation of the third embodiment.

A detailed description will be give of a method of judging the degree of contamination using the devices described above, with specific reference to a flowchart in FIG. 7 and also to Table 1.

The following description employs the following symbols:

δ1: pressure differential across the orifice 74
δ2: pressure differential across the orifice 77
δa: set pressure of pressure differential sensor 79
δb: set pressure of pressure differential sensor 78
M1: contaminant trapped by the filter 73
M2: contaminant trapped by the filter 76

The particle sizes of the contaminants M1 and M2 trapped by the filters 73 and 76, respectively, are not smaller than $K_1$ and not smaller than $K_2$, respectively. Since condition of $K_1 > K_2$ is met, the particle size distribution of the contaminant M2 includes the particle size distribution of the contaminant M1. Thus, the contaminant M1 includes particles of comparatively large particle sizes which are more liable to cause troubles in the hydraulic system, while the contaminant M2 includes all types of contaminant. When the amount of the contaminant M2 is increased to clog the filter 76, the flow rate of the oil in the conduit 75 is decreased to cause a reduction in the pressure differential across the orifice 77, and, when the set pressure δa is reached, the pressure differential sensor 79 operates. This state requires caution. When the amount of the contaminant M1 is increased to cause a clog in the filter 73, the flow rate of the oil through the conduit 72 is decreased so that the pressure differential across the orifice 74 decreases and, when the set pressure δb is reached, the pressure differential sensor 78 operates. This condition is critical for the hydraulic system. The indication is therefore conducted in the following manner. Referring to FIG. 7 showing a flow chart, in Step 111, the pressure differential $\delta 2$ is compared with the set pressure $\delta a$. When a condition of $\delta 2 > \delta a$ is met, the process proceeds to Step 112 which compares $\delta 1$ with $\delta b$. When the condition $\delta 1 > \delta b$ is met, the indication device indicates the safe condition. When the condition $\delta 1 \leq \delta b$ is met under the condition of $\delta 2 > \delta a$, the indication device indicates an abnormal state. In the event of $\delta 2 \leq \delta a$, the process proceeds to Step 113 which compares $\delta 1$ with $\delta b$. If the condition of $\delta 1 > \delta b$ is met, the indication device indicates caution, whereas, if the condition is $\delta 1 \leq \delta b$, the indication device indicates abnormality.

TABLE 1

| Judgement | Filter 73 | Filter 76 |
|---|---|---|
| Safe | O | O |
| Caution | O | X |
| Abnormal | X | O |
| Abnormal | X | X |

Table 1 shows these conditions of comparisons. Marks O and X represent, respectively, the state in which the degree of clogging of the filter is permissible and the state in which the filter has been heavily clogged. The judgment of the states, i.e., safe, caution or abnormal, is conducted by the controller and the controller delivers a signal to the indication device.

Figure 8:
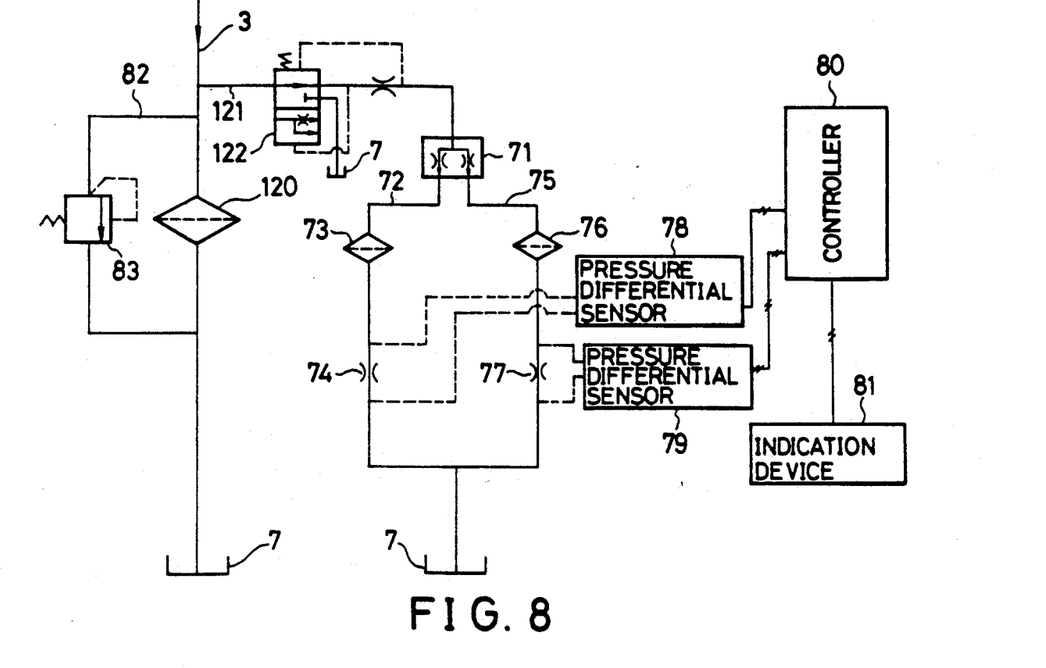
FIG. 8 is an illustration of the general arrangement of a fourth embodiment of the present invention.

FIG. 8 shows a fourth embodiment of the present invention. Returning oil flows back to the oil tank 7 through a return pipe 3 containing a filter 120. A bypass conduit 82 has a bypass valve 83. The return passage 3 is provided with a shunt pipe 121 and a flow rate control valve 122 disposed upstream of the filter 120 so that the flow of oil divided by the shunt valve 71 passes back to the oil tank 7 partly through the conduit 72 past the filter 73 and the orifice 74 and partly through the conduit 75 past the filter 76 and the orifice 77. As shown in FIG. 8, the filters 73 and 76 are in operation simultaneously. The filtration particle sizes $K_1$ and $K_2$ of the filters 73 and 76 are determined to meet the condition of $K_1 > K_2$. The inlet and outlet sides of the orifices 74 and 77 are communicated with the pressure differential sensors 78 and 79 connected to a controller 80 to which is connected also an indication device 81.

The operation is as follows. A part of the returning oil coming through the return passage 3 is made to flow through the shunt pipe 121 at a rate which is maintained constant by the flow rate control valve 122 and is divided by the shunt valve 71, so that presence of contaminant of large particle size exceeding $K_1$ and the presence of all types of contaminant of sizes greater than $K_2$ are indicated independently of each other, as explained before in connection with the first embodiment.

As has been described, according to the present invention, filters of different filtration particle sizes are arranged in series or in parallel in a circuit of working oil of a hydraulic system, and pressure differentials across the respective filters or pressure differentials of orifices connected in the circuit are detected and indicated independently. It is possible to conduct an early detection of comparatively large particles of foreign matters which tend to cause breakdown of the hydraulic system, and to grasp the degree of contamination of the working oil, thus enabling the user to take necessary countermeasure for preventing occurrence of troubles in the hydraulic system.

INDUSTRIAL APPLICABILITY

The device of the invention for indicating the degree of contamination of hydraulic circuit and the method of the invention for judging the degree of contamination can be used for protection of hydraulic devices in hydraulic circuits which incorporate filtering devices with filters, and can suitably be applied to hydraulic circuits of industrial vehicles and construction vehicles such as power shovels.

We claim:

1. Apparatus for indicating the degree of contamination of a fluid circuit by contaminant particles, said apparatus comprising:
   a plurality of filters having differing filtration particle size capability, each of said filters having an inlet and an outlet;
   conduit means for passing fluid of said fluid circuit to said plurality of filters and for receiving fluid from said plurality of filters such that said plurality of filters are in operation simultaneously,
   means associated with said plurality of filters and said conduit means to produce a plurality of output signals wherein a respective output signal is independently produced when the state of clogging for a respective one of said plurality of filters exceeds a predetermined value for that particular filter, and indicating means for receiving each of the thus independently produced output signals when it is produced, for analyzing any thus received independently produced output signals in order to classify the degree of contamination into at least three stages based on which thus independently produced output signals are present, and for indicating the state of contamination for the fluid circuit in terms of said stages.

2. Apparatus in accordance with claim 1 wherein said plurality of filters comprises a first set and a second set, with each of said first and second sets containing at least one filter, and wherein said conduit means is connected to said plurality of filters so that said first set is connected in a first flow path and said second set is connected in a second flow path which is parallel to said first flow path.

3. Apparatus for indicating the degree of contamination of a fluid circuit by contaminant particles, said apparatus comprising:
   a plurality of filters having differing filtration particle size capability, each of said filters having an inlet and an outlet,
   conduit means for passing fluid of said fluid circuit to said plurality of filters and for receiving fluid from said plurality of filters,
   means associated with said plurality of filters and said conduit means to produce a plurality of output signals wherein a respective output signal is independently produced when the state of clogging for a respective one of said plurality of filters exceeds a predetermined value for that particular filter, and
   indicating means, responsive to whether one or more of the thus independently produced output signals is present, for indicating the state of contamination for the fluid circuit,
   wherein said means associated with said plurality of filters and said conduit means to produce a plurality of output signals comprises a plurality of pressure sensors, each of said pressure sensors being connected to measure the pressure of the fluid at a respective one of the filter inlets and the filter outlets, differential pressure detection means associated with the pressure sensors to independently detect the pressure differential between the inlet and the outlet of each respective filter, means for independently comparing the thus determined pressure differential across a respective filter with a predetermined value for that particular filter representing a predetermined state of clogging for that particular filter and for independently producing an output signal when the thus determined pressure differential across that particular filter exceeds the predetermined value for that particular filter, and wherein said indicating means receives each of the thus independently produced output signals when it is produced, analyzes any thus received independently produced output signals in order to classify the degree of contamination into at least three stages based on whether one or more of the thus independently produced output signals is present, and indicates the state of contamination for the fluid circuit in terms of said stages.

4. Apparatus for indicating the degree of contamination of a hydraulic circuit, comprising:

a plurality of filters having different filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means, responsive to whether one or more of the thus independently produced output signals is present, for indicating the state of contamination for the hydraulic circuit, wherein said means associated with said plurality of filters and said conduit means to produce a plurality of output signals comprises a plurality of pressure sensors, each of said pressure sensors being connected to measure the pressure of the hydraulic fluid at a respective one of the filter inlets and the filter outlets, differential pressure detection means associated with the pressure sensors to independently detect the pressure differential between the inlet and the outlet of each respective filter, means for independently comparing the thus determined pressure differential across a respective filter with a predetermined value for that particular filter representing a predetermined state of clogging for that particular filter and for independently producing an output signal when the thus determined pressure differential across that particular filter exceeds the predetermined value for that particular filter, and wherein at least two of said plurality of filters are connected in series according to the order of filtration particle size capability such that the filter having the greatest filtration particle size capability in said series is disposed as the upstream most filter in said series.

5. Apparatus in accordance with claim 4, wherein at least three of said plurality of filters are connected in series according to the order of filtration particle size capability such that the filer having the greatest filtration particle size capability in said series is disposed upstream of the filter in said series having medium filtration particle size capability which is in turn disposed upstream of the filter in said series having the smallest filtration particle size capability.

6. Apparatus in accordance with claim 3 wherein said plurality of filters comprises a first set and a second set, with each of said first and second sets containing at least one filter, and wherein said conduit means is connected to said plurality of filters so that said first set is connected in a first flow path and said second set is connected in a second flow path which is parallel to said first flow path.

7. Apparatus in accordance with claim 6 wherein said first set comprises at least two of said filters connected in series according to the order of filtration particle size capability such that the filter having the greatest filtration particle size capability in said series is disposed as the upstream most filter in said series.

8. Apparatus for indicating the degree of contamination of a hydraulic circuit, comprising:

a plurality of filters having differing filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein at least two of said plurality of filters are connected in series according to the order of filtration particle size capability such that the filter having the greatest filtration particle size capability in said series is disposed as the upstream most filter in said series.

9. Apparatus for indicating the degree of contamination of a hydraulic circuit, comprising:

a plurality of filters having different filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein at least three of said plurality of filters are connected in series according to the order of filtration particle size capability such that the filter having the greatest filtration particle size capability in said series is disposed upstream of the filter in said series having medium filtration particle size capability which is in turn disposed upstream of the filter in said series having the smallest filtration particle size capability.

10. Apparatus for indicating the degree of contamination of a fluid circuit by contaminant particles, said apparatus comprising:

a plurality of filters having differing filtration particle size capability, each of said filters having an inlet and an outlet, conduit means for passing fluid of said fluid circuit to said plurality of filters and for receiving fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the fluid circuit;

wherein said plurality of filters comprises a first set and a second set, with each of said first and second sets containing at least one filter, and wherein said conduit means is connected to said plurality of filters so that said first set is connected in a first flow path and said second set is connected in a second flow path which is parallel to said first flow path, wherein a shunt valve is connected in said conduit means so as to divide the flow of fluid into said first flow path and said second flow path, and wherein said indicating means receives each of the thus independently produced output signals when it is produced, analyzes any thus received independently produced output signals in order to classify the degree of contamination into at least three stages based on whether one or more of the thus independently produced output signals is present, and indicates the state of contamination for the fluid circuit in terms of said stages.

11. Apparatus for indicating the degree of contamination of a hydraulic circuit, comprising:

a plurality of filters having differing filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein said plurality of filters comprises a first set and a second set, with each of said first and second sets containing at least one filter, and wherein said conduit means is connected to said plurality of filters so that said first set is connected in a first flow path and said second set is connected in a second flow path which is parallel to said first flow path, wherein said first set comprises at least two of said filters connected in series according to the order of filtration particle size capability such that the filter having the greatest filtration particle size capability in said series is disposed as the upstream most filter in said series.

12. Apparatus for indicating the degree of contamination of a hydraulic circuit, comprising:

a plurality of filters having differing filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein said plurality of filters comprises a first set and a second set, with each of said first and second sets containing at least one filter, and wherein said conduit means is connected to said plurality of filters so that said first set is connected in a first flow path and said second set is connected in a second flow path which is parallel to said first flow path, wherein said means associated with said plurality of filters and said conduit means to produce a plurality of output signals comprises a first orifice positioned in said first flow path and having an upstream side and downstream side, a second orifice positioned in said second flow path and having an upstream side and a downstream side, a plurality of pressure sensors, each of said pressure sensors being connected to measure the pressure of the hydraulic fluid at a respective one of the upstream sides and the downstream sides of the first and second orifices, differential pressure detection means associated with the pressure sensors to detect the pressure differential between the upstream side and the downstream side of each respective orifice, means for comparing the thus determined pressure differential across said first orifice with a predetermined value for said first orifice representing a predetermined state of clogging for the first set and for producing an output signal when the thus determined pressure differential across the first orifice exceeds the predetermined value for the first orifice and for comparing the thus determined pressure differential across said second orifice with a predetermined value for said second orifice representing a predetermined state of clogging for the second set and for producing an output signal when the thus determined pressure differential across the second orifice exceeds the predetermined value for the second orifice.

13. Apparatus for indicating the degree of contamination of a hydraulic circuit, comprising:

a plurality of filters having differing filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein said plurality of filters comprises a first set and a second set, wherein said conduit means is connected to said plurality of filters so that said first set is connected in a first flow path and said second set is connected in a second flow path which is parallel to said first flow path, wherein said first set contains at least one of said plurality of filters, wherein said second set contains at least two of said plurality of filters connected in series according to the order of filtration particle size capability such that the filter having the greatest filtration particle size capability in said series is disposed as the upstream most filter in said series.

14. Apparatus in accordance with claim 13, wherein said means associated with said plurality of filters and said conduit means to produce a plurality of output signals comprises a plurality of pressure sensors, each of said pressure sensors being connected to measure the pressure of the hydraulic fluid at a respective one of the filter inlets and the filter outlets of the filters in said second set, differential pressure detection means associated with the pressure sensors to detect the pressure differential between the inlet and the outlet of each respective filter in said second set, means for independently comparing the thus determined pressure differential across a respective filter with a predetermined value for that particular filter representing a predetermined state of clogging for that particular filter and for producing an output signal when the thus determined pressure differential across the particular filter exceeds the predetermined value for that particular filter.

15. Apparatus in accordance with claim 14 wherein said second set contains at least three of said plurality of filters connected in series according to the order of filtration particle size capability such that the filter having the greatest filtration particle size capability in said series is disposed upstream of the filter in said series having medium filtration particle size capability which is in turn disposed upstream of the filter in said series having the smallest filtration particle size capability.

16. Apparatus for indicating the degree of contamination of a hydraulic circuit, comprising:

a plurality of filters having differing filtration particle size capability, each of said filters having an inlet and an outlet, conduit means for passing hydraulic fluid of said hydraulic circuit to said plurality of filters and for receiving hydraulic fluid from said plurality of filters, means associated with said plurality of filters and said conduit means to produce a plurality of output signals wherein a respective output signal is independently produced when the state of clogging for a respective one of said plurality of filters exceeds a predetermined value for that particular filter, and indicating means responsive to the thus independently produced output signals for indicating the state of contamination for the hydraulic circuit, wherein said plurality of filters comprises a first set, a second set, and a third set, with each of said first, second, and third sets containing at least one filter, and wherein said conduit means is connected to said plurality of filters so that said hydraulic fluid is divided into a first flow and a second flow with said first flow going through said first set and with said second flow going through a flow rate control valve into a flow splitter to provide a third flow and a fourth flow, with said third flow going through said second set and said fourth flow going through said third set.

17. A method for judging the degree of contamination of a fluid circuit by contaminant particles, comprising:

passing fluid from said fluid circuit through a plurality of filters having differing filtration particle size capability, each of said filters having an inlet and an outlet, such that said plurality of filters are in operation simultaneously, producing a plurality of output signals wherein a respective output signal is independently produced when the state of clogging for a respective one of said plurality of filters exceed a predetermined value for that particular filter, analyzing any independently produced output signals in order to classify the degree of contamination into at least three stages based on whether one or more of the thus independently produced output signals is present, and indicating, responsive to the analysis of any thus independently produced output signals, the state of contamination for the fluid circuit in terms of said stages.

18. A method in accordance with claim 17 wherein the step of producing comprises measuring the pressure of the fluid at the filter inlets and the filter outlets of said plurality of filters having differing filtration particle size capability, determining the pressure differential between the inlet and the outlet of each respective filter of said plurality of filters having differing filtration particle size capability, independently comparing the thus determined pressure differential across a respective filter with a predetermined value for that particular filter representing a predetermined state of clogging for that particular filter, and producing an output signal when the thus determined pressure differential across that particular filter exceeds the predetermined value for that particular filter.

19. A method for judging the degree of contamination of a hydraulic circuit, comprising:

passing hydraulic fluid from said hydraulic circuit through a plurality of filters having differing filtration particle size capability, each of said filters having an inlet and an outlet, producing a plurality of output signals wherein a respective output signal is independently produced when the state of clogging for a respective one of said plurality of filters exceeds a predetermined value for that particular filter, and indicating responsive to the thus independently produced output signals the state of contamination for the hydraulic circuit, wherein hydraulic fluid is passed through at least two of said plurality of filters connected in series according to the order of filtration particle size capability such that the filter having the greatest filtration particle size capability in said series is disposed as the upstream most filter in said series.

20. A method of judging the degree of contamination of a fluid circuit, comprising:
passing fluid from said fluid circuit through a plurality of filters having differing filtration particle size capability, each of said filters having an inlet and an outlet,
producing a plurality of output signals wherein a respective output signal is independently produced when the state of clogging for a respective one of said plurality of filters exceeds a predetermined value for that particular filter, analyzing any independently produced output signals in order to classify the degree of contamination into at least three stages based on whether one or more of the thus independently produced output signals is present, and
indicating, responsive to the analysis of any thus independently produced output signals, the state of contamination for the fluid circuit in terms of said stages, and
wherein said plurality of filters comprises a first set and a second set, with each of said first and second sets containing at least one filter, and wherein the step of passing fluid comprises splitting the flow of fluid into a first flow path through said first set and a second flow path through said second set.

* * * * *